US 6,267,884 B1
Jul. 31, 2001

(54) CAPILLARY COLUMNS EMPLOYING MONODISPERSED PARTICLES

(75) Inventor: Peter Myers, Bromborough (GB)

(73) Assignee: Waters Investments Limited

( * ) Notice: Subject to any disclaimer, the term of this patent is extended or adjusted under 35 U.S.C. 154(b) by 0 days.

(21) Appl. No.: 09/477,438

(22) Filed: Jan. 4, 2000

(51) Int. Cl.⁷ .................................................. B01D 15/08
(52) U.S. Cl. ...................... 210/198.2; 210/635; 210/656; 210/502.1
(58) Field of Search .................... 210/635, 656, 210/198.2, 502.1; 96/101

(56) References Cited

U.S. PATENT DOCUMENTS

| | | | |
|---|---|---|---|
| 3,782,078 | * | 1/1974 | Jerpe ................................ 210/198.2 |
| 4,293,415 | * | 10/1981 | Bente ................................ 210/198.2 |
| 4,483,773 | * | 11/1984 | Yang ................................. 210/198.2 |
| 4,793,920 | * | 12/1988 | Cortes ............................... 210/198.2 |
| 5,246,577 | * | 9/1993 | Fuchs ................................ 210/198.2 |
| 5,858,241 | * | 1/1999 | Dittman ............................. 210/656 |
| 5,908,552 | * | 6/1998 | Dittman ............................. 210/198.2 |
| 5,935,429 | * | 8/1999 | Liao .................................. 210/198.2 |
| 5,938,919 | * | 8/1999 | Najafabadi ........................ 210/198.2 |

OTHER PUBLICATIONS

Abstract of U.S. Patent 5,858,241, Dittmann et al., Jan. 12, 1999.
Abstract of U.S. Patent 5,908,552, Dittmann et al., Jun. 1, 1999.
Abstract of U.S. Patent 5,935,429, Liao et al., Aug. 10, 1999.
Abstract of U.S. Patent 5,938,919, Najafabadi, Aug. 17, 1999.

* cited by examiner

Primary Examiner—Ernest G. Therkorn
(74) Attorney, Agent, or Firm—Brian Michaelis

(57) ABSTRACT

A capillary column comprising monodispersed particles. The capillary is formed using a suitable substrate, wherein two plates are bonded together. At least one of the plates comprises a channel where particle beads are housed. Particle bead positions are of defined and equivalent diameter are arranged along the longitudinal axis of the housing structure. These positions are used to position packing material used to occupy the column. The particle beads themselves are of equivalent diameter.

9 Claims, 4 Drawing Sheets

CAPILLARY COLUMNS EMPLOYING MONODISPERSED PARTICLES

FIELD OF INVENTION

This invention relates to a capillary liquid chromatography column comprising monodispersed particles.

BACKGROUND

The separation of molecules can be effectuated by employing liquid chromatography. A typical liquid chromatography system consists of: a column where separation of analytes is effectuated; one or more pumping units to move the solvent and sample through the column; one or more detectors to monitor the effluent exiting the column; and a data processing system used to collect and analyze data from the detector(s). A critical component of any liquid chromatography system is the column which is used to facilitate separation amongst the various analytes contained within a given sample. Liquid chromatography columns have contained within them functional chemistries which comprise the stationary phase of the column. For example, some columns have a stationary phase consisting of charged molecules, such as hydrocarbons containing an ionic moiety. In a particular instance, these ionic groups could be cations, thereby facilitating anion exchange between an anionic analyte and an anion contributed by the solvent. There are other categories of liquid chromatography columns, such as reverse phase columns. These columns typically contain a stationary phase comprising hydrocarbon functional moieties.

Analytes within a sample are introduced into a column via the solvent stream which traverses and exits the column. Based upon the chemistry of a particular analyte, and that of the stationary phase, a specific interaction between the analyte and stationary phase can occur. A critical parameter involved in this interaction is the solvent condition which provides a liquid medium carrying the sample through the column. The solvent can provide an environment which facilitates a specific interaction between an analyte and stationary phase, or it can preclude such an interaction. Those analytes that possess a relatively high affinity for the column's stationary phase will be retained on the column, while analytes with less affinity will lightly interact with the stationary phase chemistry. Alternatively, analytes with little affinity will traverse and exit the column with minimal or no interaction with the column's stationary phase. In a heterogenous sample, there will typically be a range of possible interactions between individual analytes and the stationary phase of a given column.

Capillary liquid chromatography is a micro-version of traditional liquid chromatography. As is true for traditional liquid chromatography, the column used in capillary liquid chromatography is of critical import. These columns typically have low solvent consumption and require low volumes of sample for analysis. These conditions translate into a higher degree of separation efficiency. Capillary liquid chromatography systems typically comprise a micropumping unit, a capillary column, a detector, and a data processing system.

Capillary liquid chromatography columns are typically produced using such materials as fused silica, stainless steel, or polymeric compositions. The lumen of the capillary is packed with packing material containing separation material, such as bonded silica particles. Typically, the internal diameter of the capillary column is between 50 and 500 $\mu$m. Great variability exists between columns due to current manufacturing practice which significantly impacts negatively upon chromatographic reproducibility from column to column. For example, the particles used in the packing material used to pack a column are generally not monodispersed throughout the column, instead, there is typically a particle size distribution throughout the capillary column.

SUMMARY OF THE INVENTION

The present invention provides monodispersed capillary liquid chromatography columns, which increase column separation efficiency and enhance reproducibility between manufactured columns. This increase fidelity in reproducibility between capillary columns will greatly contribute to the practitioner's ability to perform reliable and meaningful capillary chromatography.

According to the invention, the capillary column comprising monodispersed particles is formed using a suitable substrate. The capillary column is constructed of a housing having a first plate and a second plate. In the first plate a channel is formed. The dimensions (e.g. diameter) of the channel are equivalent to the dimensions (e.g. diameter) of monodispersed particle beads used to populate the channel. The channel constitutes the lumen of the capillary column. A set of indentations is positioned along the interior longitudinal axis of the capillary column's channel at intervals corresponding to approximately half the diameter of the particle bead used to pack the column. These indentations are used in order to stabilize the positioning of the particle bead once disposed within the channel. At least one particle bead is positioned between a set of indentations. A cover plate, that is, the second plate, is positioned and bonded to the first plate in such a manner as to securely cover the lumen or channel of the first plate. In another embodiment, The first and second plate comprise an internal cavity forming a channel.

Another embodiment of the present invention includes an axial gradient capillary column. In this embodiment of the invention, particle beads of different surface chemistries are used to populate the capillary column. For example, particle beads with $C_{18}$ chemistry are disposed within one or more indents located along the interior longitudinal axis of the capillary column, that is, the channel, followed by the occupancy of particle beads having $C_8$ chemistry within one or more indents located along the same channel. Only two chemistries are used for illustrative purposes, however, more than two sets of chemistries can be employed in forming an axial gradient capillary column.

In a further embodiment of the instant invention, the diameter of the capillary column's channel is increased to "nd", where "n" is an integer and "d" is the diameter of the bead. For example, if n=2, then the particle beads are placed in the channel forming a 2:1:2:1 etc. geometry. Specifically, two beads occupy a first position followed by one bead occupying a next position, etc. along the longitudinal axis of the channel of the first plate. However, as the channel increases from one dimension to two dimensions and above, with respect to bead geometry within the channel, a radial and axial gradient capillary column can be constructed. The radial gradient can be formed by applying, for example, a $C_8$ chemistry bead next to a $C_{18}$ chemistry bead perpendicular to the longitudinal axis of the channel. Such a configuration focuses the parabolic flow profile of the mobile phase to produce a flat flow profile, thereby increasing the column's efficiency. Features of the invention include provision of a monodispersed column that is readily reproduced.

DETAILED DESCRIPTION

Figure 1:
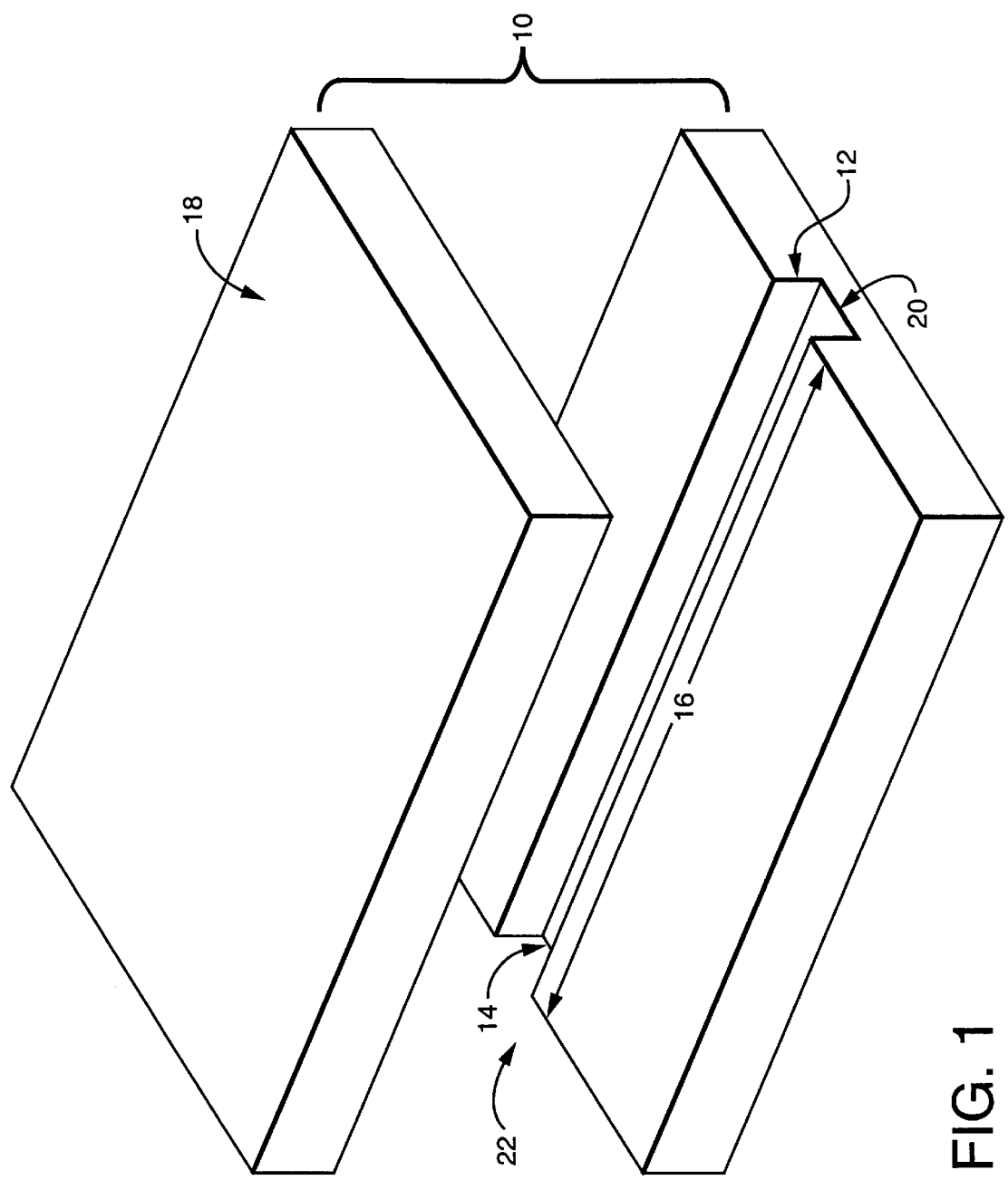
FIG. 1 is an illustration of a capillary column comprising two plates.
Figure 2:
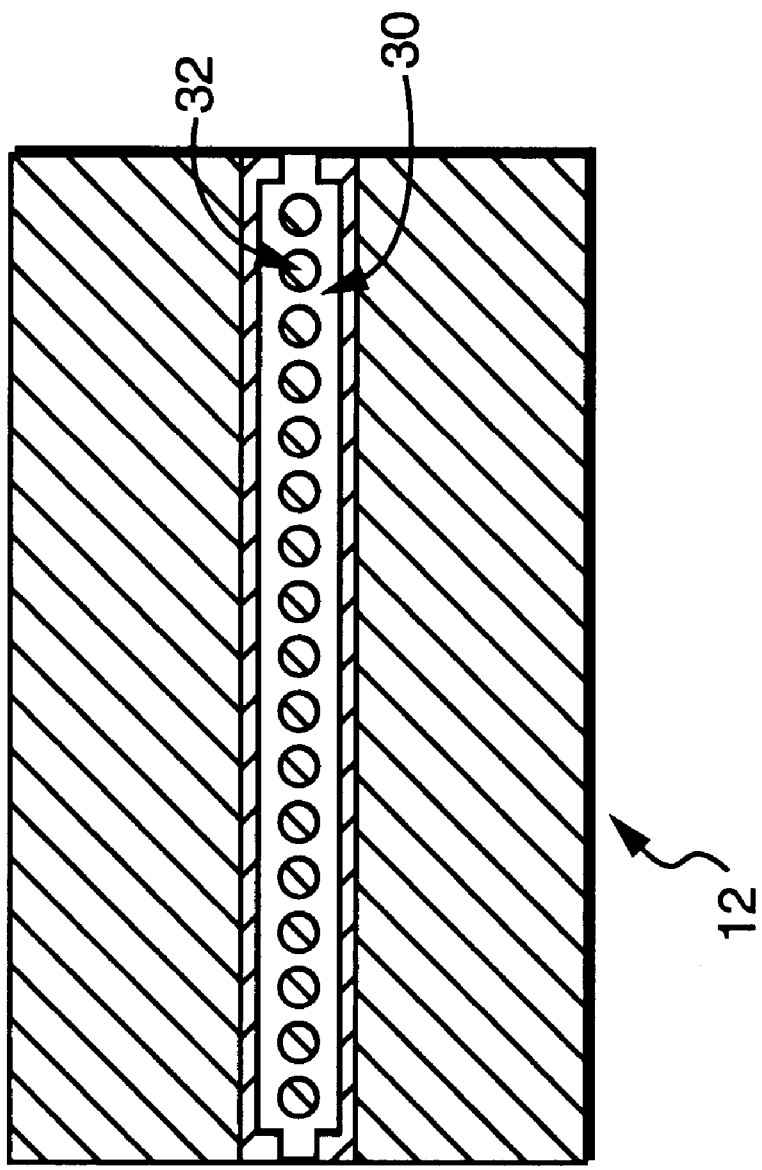
FIG. 2 is an illustration of a first plate containing a channel.

Referring now to FIG. 1, the present invention pertains to a capillary column 10 comprising monodispersed particles. The capillary column 10 is formed using a suitable substrate. See FIG. 1. The capillary column 10 comprises a housing structure (or simply "housing") further comprising a first 12 and a second plate 18. The first plate 12 further comprising an internal cavity 14 forming a lumen or channel 14 within the first plate 12, and hence the capillary column 10. The first plate 12 comprises a first end 20 and second end 22 as well as a longitudinal axis 16. The diameter of the channel 14 approximates the diameter of the packing particle beads 32 that are to be used to pack the channel 14 of the first plate 12. See FIG. 2. Indentations 30 are located along the longitudinal axis 16 of the channel 14 of the first plate 12. The diameter of an indent 30 approximates half of the diameter of a particle bead 32 used to pack the column 10. Indents are positioned corresponding to approximately half the diameter of the particle bead 32 in order to stabilize the particle bead once disposed into the indent 30. A cover plate, or second plate, 18 is then positioned and securely bonded to the first plate 12.

In another embodiment, both the first 12 and second 18 plate have a channel 14 in which particle beads 32 are placed. In this embodiment, one or both of the plates contain indentations 30 to stabilize the particle bead 32. This embodiment also consists of two ends 12 and 22, wherein no frit is needed due to both ends having a smaller diameter than the lumen of the channel 14. The first 12 and second 18 plate are bonded after placement of the particle beads 32 into their respective positions.

The bonding of the first plate 12 to the second plate 18 can be accomplished by any means known to those skilled in the art that will securely bond the two plates together in such a manner as to form a liquid tight seal between the two plates. The bonding occurs after the placement of the particle beads 32 within the their respective particle bead positions within the channel 14. Means for placing the particle bead within its respective position is well known to those of skill in the art. A sealer can be used prior to bonding the first 12 and second 18 plates. Means for bonding include, but are not limited to, use of an adhesive agent, securing the two plates by use of a screw and nut configuration, or equivalents thereto.

A suitable substrate used to form a liquid chromatography capillary column housing structure includes silica based material, such as fused silica and glass, polymeric material, such as PEEK (polyetheretherketone), or any plastic material that can withstand the pressure and solvent of an High Performance Liquid Chromatography (HPLC) system. The actual manipulation of the capillary material to form a capillary column 10 is well known to those in the art. The length of a capillary column 10 is from about 1 to about 25 cm. The lumenal 14 (or channel) diameter of the capillary column 10 is consistent with the diameter of the particle bead 32 that is to be used to pack the column 10. The present invention encompasses particle beads 32 having a diameter from about 100 to about 500 $\mu$m.

The capillary column 10 in the instant invention contains one or more indentations 30 that lie along the longitudinal axis 16 of the first plate 12 at determined locations within the channel 14. The longitudinal axis 16 of the first plate 12 is defined by the axis that lies between the first end 20 and second end 22. The positioning of the indentations 30 is defined by approximately half the diameter of the particle bead 32 to be used in the column 10. The indentations 30 are positioned at intervals calculated using the approximate half diameter of the particle bead 32 to be used, such that the distance between subsequent indentations 30 is approximately half the diameter of the particle bead 32 used to occupy the column 10. The particle beads 32 of the present invention are of substantially uniform (and equivalent) dimensions, and therefore, the indentations 30 are positioned at approximately uniform intervals. Methods used to produce the indentations 30 are well known to those skilled in the art. These indentations 30 are used to stabilize the position of the particle bead 32 once in their respective position. These indentations arise from the interior surface of the lumen 14 and extend into the lumen (or channel) 14.

Figure 3:
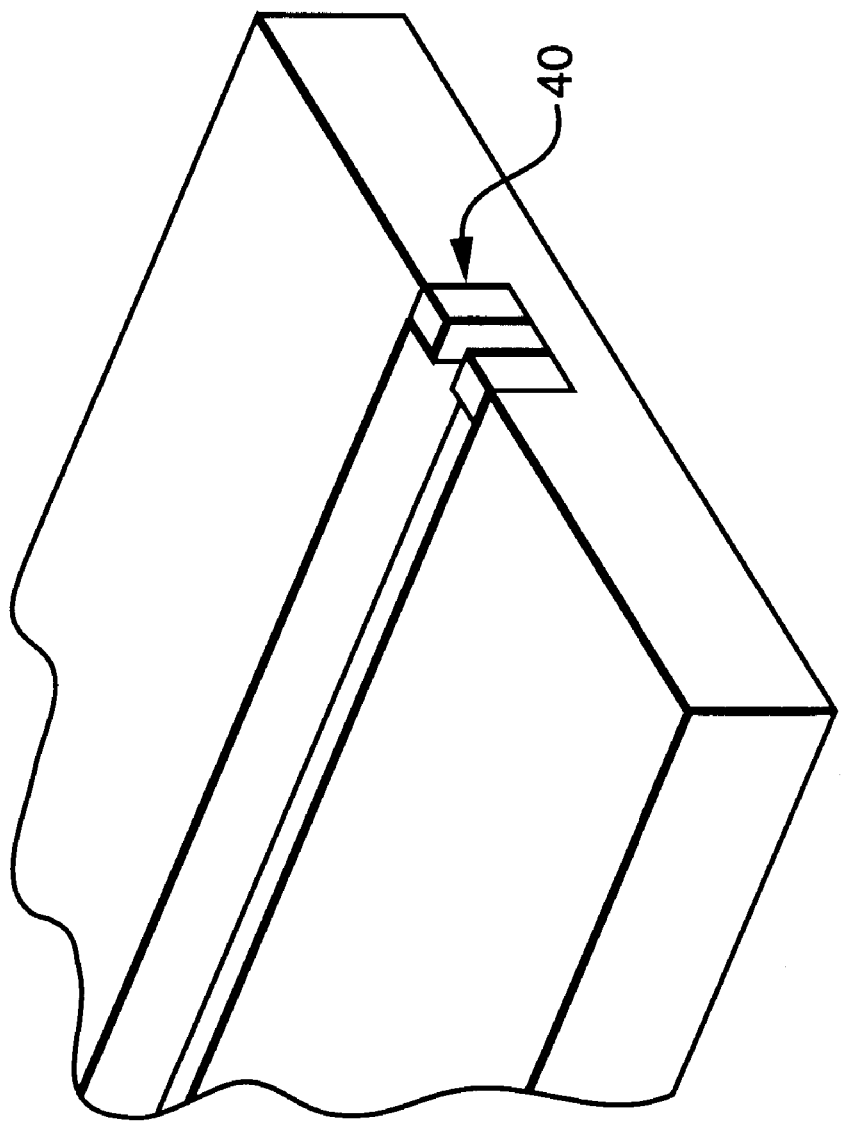
FIG. 3 is an illustration of an end of the channel.

Prefabricating molding methods well known to those skilled in the art can be employed to produce a capillary column 10 with predetermined indentations 30 positioned along the interior longitudinal axis 16 of the column's channel 14. In one embodiment of the present invention, no inlet or exit frits are required as both the inlet and exit of the capillary column 10 are slightly smaller in diameter than the remaining lumen 14 of the capillary column 10. See FIG. 3.

Suitable liquid chromatography capillary column packing material includes silica, aluminum and organic polymers. The present invention encompasses particle beads 32 with diameters ranging from about 100 to about 500 $\mu$m. In the instant invention the particle beads 32 are monodispersed, that is, the particle beads 32 occupying the column 10 are of approximately equivalent dimension. These particle beads 32 are disposed in the indentations 30 located along the lumenal compartment 14 of the column 10. The particle bead 32 can contain homogenous functional groups, for example, the surface chemistry (or functional group constituent) of a particle bead could be a $C_{18}$ moiety.

Figure 4:
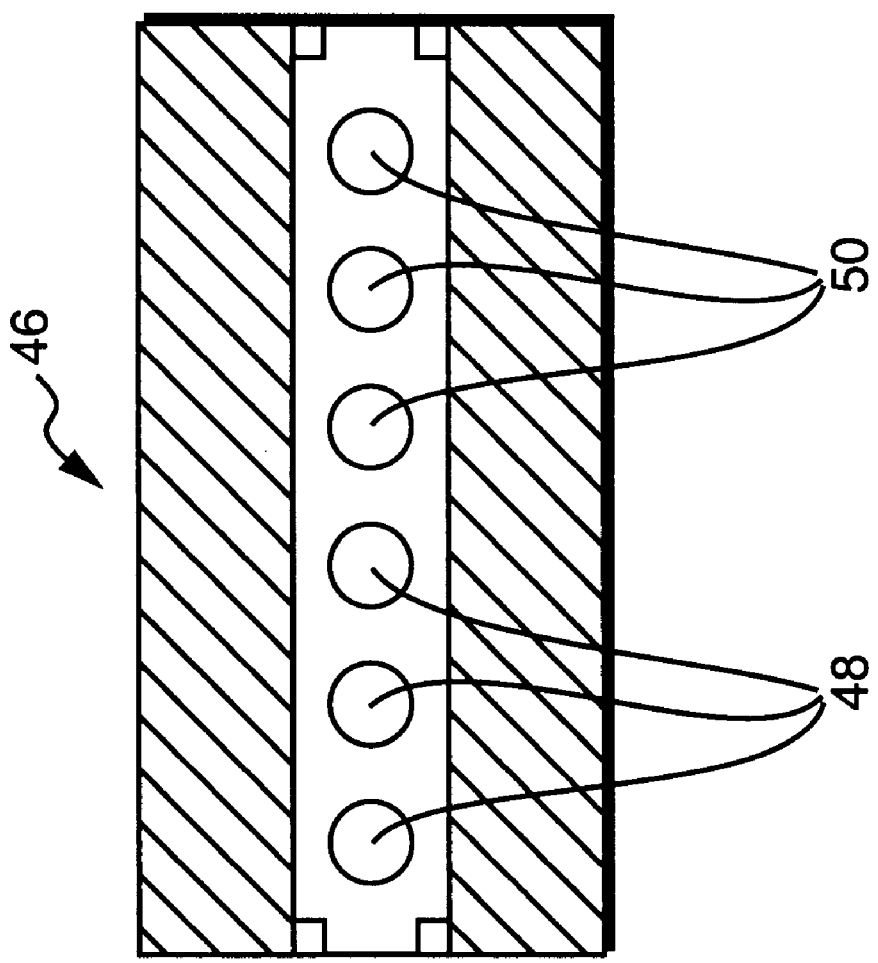
FIG. 4 is an illustration of an axial gradient capillary column according to the invention.

In another embodiment of the invention illustrated in FIG. 4, an axial gradient capillary column 46 is disclosed. Particle beads of different surface chemistries are disposed in different positions 48, 50. For example, particle beads containing a $C_{18}$ chemistry can be disposed within one or more positions 48 of the column. In addition to the $C_{18}$ beads, for example, $C_8$ beads can be disposed in other positions 50. The placement of the different particle chemistry beads will facilitate a gradient like arrangement with respect to the particular chemistries involved., For example in this illustrative example, a gradient of increasing (or decreasing, depending upon the arrangement of the particles along the longitudinal axis) hydrophobic environment is established. In the present invention, more than two different surface chemistries can be employed in forming an axial gradient capillary column 46.

In still another embodiment of the instant invention, the diameter of the channel is increased to include a radial arrangement of particle beads, thereby allowing for a radial and axial gradient capillary column. The diameter of the channel is denoted as "nd", where "n" is an integer and "d" is the diameter of the particle beads to be used in the column. For example, if n=2, then the beads occupy the channel forming a 2:1:2:1 etc. configuration, wherein the number refers to the number of particle beads. In this particular configuration, two particle beads occupy a first position followed by only one bead occupying a subsequent position and so on. It should be appreciated that "n" need not be restricted to "2" it can be other integers. In this illustrative embodiment, the term "n" can have a range from about 1 to about 20. For example, if n=3, then the particles are placed in the channel forming a 3:2:3:2 etc. geometry. In this embodiment, a two-way gradient capillary column is established. A radial gradient can be configured together with an axial gradient in this embodiment. For example, a $C_8$ chemistry bead can be positioned proximate to a $C_{18}$ chemistry bead disposed perpendicular to the longitudinal axis of the channel. Therefore, a two-way gradient is established. Such a configuration will focus the parabolic flow profile of the mobile phase to produce a flat flow profile, thereby increasing the column's efficiency.

While this invention has been particularly shown and described with reference to embodiments thereof, it will be understood by those skilled in the art that various changes in form and details may be made therein without departing from the spirit and scope of the invention as defined by the appended claims.

What is claimed is:

1. A liquid chromatography column for capillary chromatographic analysis, comprising a housing structure, wherein said housing structure comprises a first plate and a second plate, wherein said first plate further comprises an interior channel having a first and second ends and a longitudinal axis;

one or more indentations aligned along said longitudinal axis of said interior channel; and a packing material disposed within said interior channel, wherein said packing material comprises particle beads having approximately equivalent dimensions, and wherein a diameter of said one or more indentations approximates half that of said particle beads.

2. The liquid chromatography column of claim 1, wherein suitable material used to form said housing structure is any material in which a channel can be cut or molded and can withstand HPLC pressures and solvents.

3. The liquid chromatography column of claim 2, wherein said suitable material used to form said housing structure is selected from the group consisting of fused silica, glass, and polymeric material.

4. The liquid chromatography column of claim 3, wherein said polymeric material is PEEK (polyetheretherketone).

5. The liquid chromatography column of claim 1, wherein a length of said column ranges from about 1 to about 25 cm.

6. The liquid chromatography column of claim 1, wherein said packing material is selected from the group consisting of silica, aluminum and organic polymers.

7. The liquid chromatography column of claim 1, wherein said diameter of said particle bead ranges from about 100 to about 500 $\mu$m.

8. The liquid chromatography column of claim 1, wherein said first and second plates comprise a channel.

9. An axial gradient capillary column, comprising:

a housing structure, wherein said housing structure comprises a first plate and a second plate, wherein said first plate further comprises an interior channel having a first and second ends and a longitudinal axis;

one or more particle bead positions aligned along said longitudinal axis of said interior channel defined by one or more indentations; and a heterogenous packing material disposed within one or more positions, wherein said heterogenous packing material comprises particle beads having an equivalent diameter but different surface chemistries, wherein said particle beads are disposed within said one or more particle bead positions in such a manner as to facilitate a gradient of said surface chemistry along said longitudinal axis of said interior channel, and wherein a diameter of said one or more indentations approximates half of said known diameter of said particle beads.

* * * * *